(12) United States Patent
Durairaj et al.

(10) Patent No.: US 6,350,921 B1
(45) Date of Patent: Feb. 26, 2002

(54) PROCESS FOR THE PRODUCTION OF A DIHYDROXYBENZENE AND DICARBINOL FROM DIISOPROPYLBENZENE

(75) Inventors: Raj B. Durairaj, Monroeville; Vaughn J. Romell, Pittsburgh; Michael N. Tackie, Murrysville, all of PA (US); Thomas K. Volek, Tuscaloosa, AL (US)

(73) Assignee: Indspec Chemical Corporation, Pittsburgh, PA (US)

( * ) Notice: Subject to any disclaimer, the term of this patent is extended or adjusted under 35 U.S.C. 154(b) by 0 days.

(21) Appl. No.: 09/034,143

(22) Filed: Feb. 24, 1998

(51) Int. Cl.[7] ................................................ C07C 37/60
(52) U.S. Cl. ...................... 568/771; 568/741; 568/768; 568/803
(58) Field of Search ................................ 568/741, 771, 568/768, 803

(56) References Cited

U.S. PATENT DOCUMENTS

| | | | |
|---|---|---|---|
| 2,856,432 A | | 10/1958 | Conner, Jr. et al. |
| 3,883,600 A | * | 5/1975 | Miller ........................ 260/610 |
| 3,923,908 A | | 12/1975 | Suda et al. |
| 3,932,528 A | | 1/1976 | Suda et al. |
| 3,953,521 A | | 4/1976 | Suda et al. |
| 3,953,528 A | | 4/1976 | Inada et al. |
| 3,978,142 A | * | 8/1976 | Burkholder ................. 260/621 |
| 4,059,637 A | | 11/1977 | Hosaka et al. |
| 4,237,319 A | | 12/1980 | Nambu et al. |
| 4,267,387 A | | 5/1981 | Imai et al. |
| 4,283,570 A | | 8/1981 | Nakagawa et al. |
| 4,339,615 A | | 7/1982 | Imai et al. |
| 4,835,325 A | | 5/1989 | Miki et al. |
| 4,847,436 A | | 7/1989 | Wu |
| 4,847,437 A | | 7/1989 | Wu |
| 4,849,549 A | | 7/1989 | Wu |
| 4,935,551 A | | 6/1990 | Wu |

FOREIGN PATENT DOCUMENTS

| | | |
|---|---|---|
| CA | 586534 | 11/1959 |
| GB | 727498 | 4/1955 |
| GB | 743736 | 1/1956 |
| GB | 819450 | 9/1959 |
| GB | 921557 | 3/1963 |
| JP | 56-020532 A | 2/1981 |

* cited by examiner

Primary Examiner—James O. Wilson
Assistant Examiner—Howard V. Owens, Jr.
(74) Attorney, Agent, or Firm—Debra Z. Anderson; Diane R. Meyers; Eckert Seamans Cherin & Mellott, LLC (57) ABSTRACT

Improved methods for the simultaneous production of dihydroxybenzene and dicarbinol from diisopropylbenzene are provided. These methods provide for continuous and simultaneous production of diisopropylbenzene dihydroperoxide (DHP) and diisopropylbenzene hydroxyhydroperoxide (HHP) using Karr Column extractors operated in series. A very high purity DHP-containing solution, the precursor to the dihydroxybenzene, can be produced according to the reported methods. A safe and efficient method for producing dicarbinol from HHP is also disclosed.

27 Claims, 1 Drawing Sheet

PROCESS FOR THE PRODUCTION OF A DIHYDROXYBENZENE AND DICARBINOL FROM DIISOPROPYLBENZENE

FIELD OF THE INVENTION

The present invention relates to an improved process for the continuous simultaneous production of dihydroxybenzene (DHB) and diisopropylbenzene dicarbinol (DCL) from diisopropylbenzene. More specifically, this process includes the steps of: oxidizing diisopropylbenzene to obtain an oxidate comprising, among other things, diisopropylbenzene dihydroperoxide (DBP) and diisopropylbenzene hydroxyhydroperoxide (HHP); extracting DHP and HHP from the oxidate into an aqueous caustic solution using a Karr Column operation; continuously and simultaneously isolating HHP and DHP into separate fractions from the caustic solution by using Karr Column cold and hot methyl isobutyl ketone (MIBK) extractions; producing dihydroxybenzene by the cleavage of the DHP extract fraction in the presence of an acid catalyst; and producing dicarbinol by decomposing the HHP fraction under atmospheric conditions using an aqueous alkaline solution.

BACKGROUND OF THE INVENTION

It is known in the art that hydroperoxides, such as diisopropylbenzene dihydroperoxide (DHP), diisopropylbenzene monohydroperoxide (MHP), and diisopropylbenzene hydroxyhydroperoxide (HHP), can be produced by oxidizing diisopropylbenzenes with molecular oxygen either in the presence or absence of base catalysts. The continuous oxidation and production of diisopropylbenzene dihydroperoxide from the diisopropylbenzenes in the presence of a strong base, such as sodium hydroxide, are disclosed, for example, in British Patent No. 727,498 and U.S. Pat. No. 3,953, 521. These patents disclose that m- and p-diisopropylbenzene dihydroperoxides can be continuously isolated from the diisopropylbenzene oxidation mixture by caustic extraction, and that continuous oxidation of diisopropylbenzenes for the production of dihydroperoxides can be achieved by maintaining the pH in a range of between 8 and 11 and the temperature at about 85–95° C. in the oxidation reactor. British Patent No. 727,498, as well as U.S. Pat. No. 2,856,432, also disclose that the dihydroperoxides (DHP) present in the diisopropylbenzene oxidation mixture can be effectively separated by means of 4–8 wt. % caustic solutions. In addition to dihydroperoxide (DHP), part of the hydroxyhydroperoxide (HHP) present in the oxidation material is also extracted into the caustic solution.

U.S. Pat. No. 4,237,319 also discloses a method for the batch production of m-diisopropylbenzene dihydroperoxide (m-DHP) by oxidizing m-diisopropylbenzene under alkaline conditions.

Extraction of DBP into the caustic solution, as described in the above art, can be followed by isolation of the DHP for the production of a dihydric phenol, such as resorcinol or hydroquinone, in several ways. Of these methods, a preferred method in the art is to extract the DHP from the caustic solution into an organic solvent, preferably MIBK. Using this solvent, a temperature of 70–80° C. and contact times of 5–10 minutes, it is possible to extract a high proportion of the DHP into MIBK with negligible losses by decomposition. British Patent No. 921,557 discloses that m-DHP present in the aqueous caustic solution is extracted by the MIBK solvent at 75° C. In order to improve the extraction efficiency, U.S. Pat. No. 3,932,528 discloses that by adding about 1% ammonia into an aqueous 8% caustic soda solution containing 12.3% DHP, MIBK solvent is more effective at 60° C. for DHP extraction through three countercurrent contact stages.

U.S. Pat. No. 4,059,637 describes a method by which DHP present in the caustic solution is extracted using MIBK solvent in a four-stage countercurrent mixer settler-type extraction. The caustic solution containing DHP used in the mixer settler-type extraction is previously treated with MIBK at a temperature of below 30° C. to remove oxidation by-products having 2-hydroxy-2-propyl group such as diisopropylbenzene hydroxyhydroperoxide (HHP) and diisopropylbenzene dicarbinol (DCL). The HHP content of the caustic solution containing DHP prior to feed into the mixer-settler extraction is reported to be about 4.2%. After the extraction, the purity of DHP in the MIBK solution is reported to be 93%.

Several patents disclose different acid type catalysts and temperatures to obtain a dihydric phenol such as resorcinol or hydroquinone from the DHP by cleavage. For example, British Patent No. 743,736 discloses sulfuric acid as the catalyst for m-DHP cleavage in the presence of an MIBK solvent under reflux conditions. With a residence time of between about 7.5–10 minutes and a 0.2 wt. % $H_2SO_4$ catalyst, 99.6% of the DHP is decomposed. British Patent No. 819,450 discloses a sulfur trioxide catalyst for the cleavage of m-DHP; sulfur trioxide is reported as causing a far more rapid cleavage reaction than the corresponding quantity of sulfuric acid. The decomposition of m-DHP is carried out continuously in two reactors connected in series, using MIBK and acetone as the solvents employed in the cleavage operation. Canadian Patent No. 586,534 also discloses the use of a sulfur trioxide catalyst for cleaving m-DHP in the presence of 0.3 wt. % water in the cleavage reaction. U.S. Pat. No. 3,923,908 discloses a process for cleaving diisopropylbenzene dihydroperoxides in the presence of impurities such as isopropylphenyl dimethylcarbinol (MCL), diisopropylbenzene hydroxyhydroperoxide (HHP) and diisopropylbenzene dicarbinol (DCL) using a sulfur trioxide catalyst and a solvent.

In order to effectively utilize the by-product diisopropylbenzene hydroxyhydroperoxide (HHP), Japanese Patent Application 95-304027 and Japanese Patent Application No. 95-301055 disclose a method by which an MIBK solution containing HHP is reduced by hydrogen in the presence of a palladium-alumina catalyst (a material carrying 1 wt. % of palladium metal) in an autoclave equipped with an agitator, at a hydrogen pressure of 6 atmospheres and a reaction temperature of 90° C., to obtain diisopropylbenzene dicarbinol (DCL). Though this method produces DCL from HHP, the safety of this process is questionable, as it involves handling high pressure hydrogen in the presence of a highly volatile solvent (MIBK) at high temperatures.

One important aspect recognized in the art of producing high purity dihydric phenol by the hydroperoxidation technology is to prepare a high purity cleavage feed (DHP) from the diisopropylbenzene oxidation mixture. Although DHP is produced in the DIPB oxidation, it may not be easy to completely remove the DHP from the oxidation mixture for use in the cleavage step of the hydroperoxidation process. In a standard first step of DHP separation from the oxidate, caustic extraction is typically performed using either a 4% or 8% NaOH solution. During this extraction, DHP as well as other impurities present in the oxidate, such as HHP, acetylisopropylbenzene hydroperoxide (KHP), MHP, etc., are extracted. When an 8% NaOH solution is used, about 90–95% of the HHP and KHP present in the oxidation mixture are known to be extracted into the caustic solution, along with about 1–2% MHP. MHP present in the caustic solution is back extracted with a DIPB solvent. The solution comprising the DIPB, extracted MHP and other extracted oxidation impurities can then be recycled to the oxidation reaction and subjected to oxidation. This DIPB extraction does not have much effect on removing other impurities such as HHP and KHP from the caustic extract solution, however. To remove the HHP from the caustic solution, an MIBK solvent extraction is typically done at a low temperature. In spite of this operation, the concentration of HHP in the caustic solution before the final MIBK extraction can still be relatively high and, therefore, this method has been found to be a difficult route to produce a very high purity DHP for the cleavage. None of the patents or other literature in the art suggest or disclose what happens to impurities such as KHP present in the caustic extract. If the extraction procedures or methods are not efficient, then the hydroperoxidation process impurities are expected to interfere with the isolation of a very high purity DHP needed for a highly efficient cleavage operation. None of the art teaches or suggests a process by which, in a continuous operation, a very high purity DHP can be produced from the diisopropylbenzene oxidation materials.

In an attempt to make a high purity DHP material, U.S. Pat. No. 4,059,637 describes a method in which four mixer-settler type extractors are used. The DHP-containing caustic solution used in the '637 patent contained DHP and HHP in a ratio of about 95.8:4.2, even after the MIBK extraction was performed at 20° C. on the solution. According to this patent, this cold MIBK extraction of the caustic extraction was done separately as a discontinuous process rather than being integrated with the mixer-settler extraction operation. This procedure produced a low purity DHP-containing product for the cleavage reaction.

Thus, the techniques used in the art to separate a high purity DHP from the DIPB oxidation materials have disadvantages. No single process completely describes a continuous method of obtaining a high purity DHP from the oxidate, while identifying and characterizing the nature of impurities extracted into the caustic and MIBK extractions. In addition, art-described methods for preparing DCL from DIPB oxidation materials give rise to safety concerns. There remains a need, therefore, for such a process which provides for the safe and efficient preparation of products such as a high purity DHP feed for use in preparation of DHB, as well as DCL.

SUMMARY OF THE INVENTION

The present invention has met the above described needs by providing a novel process for the preparation of a dihydric phenol, such as resorcinol or hydroquinone, from a high purity DHP-containing cleavage feed while also effectively utilizing the HIP impurity in the oxidation product of DIPB for the manufacture of dicarbinol. This method generally comprises the steps of oxidizing diisopropylbenzenes with molecular oxygen in the presence of a base catalyst to obtain an oxidation reaction mixture, also referred to herein as "oxidate", comprising, among other things, diisopropylbenzene dihydroperoxide (DHP) and diisopropylbenzene hydroxyhydroperoxide (HHP); feeding the oxidate into a Karr Column, also referred to herein as a "caustic extraction column"; continuously and simultaneously extracting DHP and HHP from the oxidate in a counter-current operation; continuously generating a DHP/HHP enriched caustic, also referred to herein as "rich caustic", and a recycle stream, which recycle stream can be directly fed back into the oxidation reactor; continuously feeding the rich caustic into a second Karr Column, also referred to herein as "cold MIBK column", for the simultaneous and continuous generation of DHP enriched caustic and the separation of HHP from the DHP enriched caustic achieved by performing this MIBK extraction operation at a low temperature, also referred to herein as "cold MIBK extraction"; continuously feeding the DHP enriched caustic into a third Karr Column, also referred to herein as "hot MIBK column", for the continuous generation of a very high purity DHP to obtain an MIBK solution, herein referred to as "hot MIBK solution", for feeding to a cleavage step for continuous generation of dihydroxybenzene and continuous generation of a lean caustic containing very low levels of unextracted hydroperoxides. Prior to cleavage, the hot MIBK solution is preferably concentrated; the concentrate is then fed into a continuous cleavage reactor where DHP is cleaved in the presence of a catalyst to produce the corresponding dihydric phenol, such as resorcinol or hydroquinone, and acetone. The HHP present in the cold MIBK extract obtained following the second Karr Column extraction is decomposed by treatment with an aqueous alkaline solution under atmospheric and aqueous conditions to obtain the corresponding dicarbinol.

It is, therefore, an object of the present invention to provide an improved process for the production of polyphenols, such as resorcinol or hydroquinone, and dicarbinol from diisopropylbenzenes.

A further object of the present invention is to provide a process for the continuous separation of DHP from the DIPB oxidation material and generation of an oxidation recycle feed and a rich caustic stream from the caustic extraction using Karr Column operations.

A further object of the present invention is to provide a process for the continuous and highly efficient separation of the impurities such as HHP, KHP, MHP, and other oxidation impurities from the DHP/HHP rich caustic stream by performing a cold temperature MIBK extraction in a Karr Column.

Another object of the invention is to provide a process for production of a DHP enriched caustic for high temperature MIBK extraction in a Karr Column.

Another object of the invention is to provide a process for the continuous production of a very high purity DHP material feed for the cleavage step of the hydroperoxidation process by performing MIBK extractions on the caustic extract solution using Karr Column operations.

Still a further objective of this invention is to provide an aqueous, nonhydrogenated, safe, effective and efficient process for the conversion of HHP to DCL.

These and other objects of the invention will be apparent from the following description of the invention.

DETAILED DESCRIPTION OF THE INVENTION

The present invention is directed to a method for manufacturing dihydroxybenzene and dicarbinol from diisopropylbenzene comprising: a) oxidizing diisopropylbenzene with oxygen in the presence of a base catalyst to obtain an oxidation reaction mixture or "oxidate" comprising diisopropylbenzene dihydroperoxide (DHP), diisopropylbenzene hydroxyhydroperoxide (HHP), acetyl-isopropylbenzene hydroperoxide (KHP), and one or more members selected from the group consisting of diisopropylbenzene monohydroperoxide (MHP), isopropylbenzene monocarbinol (MCL), diisopropylbenzene dicarbinol (DCL), acetyl-isopropylbenzene monocarbinol (KCL) and other organic peroxides; b) feeding the oxidate, a caustic solution and an organic solvent into a caustic extraction Karr Column; c) continuously and simultaneously generating two streams from the caustic extraction Karr Column of step b), the first caustic extraction stream comprising DBP, HHP and KHP extracted in a countercurrent operation, and the second caustic extraction stream comprising one or more members selected from the group consisting of MHP, MCL, DCL, KCL, other organic peroxides, the organic solvent fed to the caustic extraction Karr Column and diisopropylbenzene; d) continuously feeding the first caustic extraction stream from step c), an organic solvent cooled to a temperature between about 10 and 30° C., and an alkaline solution into a second Karr Column; e) continuously and simultaneously generating two streams from the second extraction Karr Column, the first cold extraction stream comprising a cold organic solution comprising HHP and KHP and the second cold extraction stream comprising DBP enriched caustic; f) continuously feeding the DHP enriched caustic of step e) and an organic solvent that has been heated to a temperature of between about 40 and 85° C. into a third extraction Karr Column; g) generating two streams from the third extraction Karr Column, the first stream comprising a hot organic solution comprising high purity DHP and the second comprising lean caustic comprising low levels of unextracted hydroperoxides; h) concentrating the hot organic solution of step g) and feeding the concentrate into a continuous cleavage reactor where DHP is cleaved in the presence of an acid catalyst to produce a solution comprising the corresponding dihydroxybenzene and acetone; and i) decomposing the HHP present in the cold organic extract of step e) by treatment with an aqueous sodium solution under non-hydrogenated atmospheric pressure and aqueous conditions to obtain the corresponding dicarbinol.

The process for the production of a dihydric phenol, such as resorcinol or hydroquinone, and dicarbinol according to the present invention generally involves the production of diisopropylbenzene dihydroperoxide (DHP) and diisopropylbenzene hydroxyhydroperoxide (HHP) from diisopropylbenzene (DIPB) and the subsequent conversion of the DHP to the corresponding dihydric phenol and the HHP to the corresponding dicarbinol. Preferably the DIPB used herein, and from which the DHP and HHP are produced, is either m-diisopropylbenzene (m-DIPB), p-diisopropylbenzene (p-DIPB), or mixtures thereof.

The oxidation of the DIPB, such as m-DIPB or p-DIPB, is generally carried out in the liquid phase in the presence of an oxygen containing gas, which may be either pure oxygen, such as molecular oxygen, or a mixture containing oxygen, such as air. The oxidation reaction can be carried out in either a continuous or batchwise method, depending on the needs and preferences of the user. This oxidation reaction can be carried out in the presence or absence of one or more base catalysts; preferably, a base catalyst such as sodium hydroxide or sodium carbonate is used. The presence of these basic substances in the oxidation reaction increase the efficiency of the oxidation, such as by enhancing the rate of oxidation by retarding the development of excessive acidity due to the formation of carboxylic acids, including but not limited to formic acid, acetic acid, and the like, which hinder the oxidation reaction. The preferred pH for the oxidation reaction is in the range of about 7 to 11. The DIPB oxidation product obtained, for example, by the continuous oxidation process described in British Patent No. 727,498 or by the batch oxidation process described in U.S. Pat. No. 4,237,319, is suitable for use in the methods of the present invention; DIPB oxidation methods taught in other patents or publications can also be used, including, but not limited to, the anhydrous, non-alkaline process taught in U.S. Pat. No. 4,935,551.

The oxidation reaction may be conducted over a wide range of temperatures, preferably between about 80 and 120° C. For practical purposes, when the reaction is conducted in the presence of an aqueous caustic solution, the oxidation reaction is preferably run at about 90° C.±5° C. and at about 20–80 psi pressure.

Oxidation of DIPB results in an oxidate comprising both the desired DHP and HHP in addition to numerous oxidation by-products. These by-products include, for example, hydroperoxides such as isopropylbenzene monohydroperoxide (MHP) and acetyl-isopropylbenzene hydroperoxide (KHP); carbinols such as isopropylbenzene monocarbinol (MCL) and diisopropylbenzene dicarbinol (DCL); ketones such as acetyl isopropylbenzene (MKT) and acetyl-isopropylbenzene monocarbinol (KCL); and other organic peroxides formed from the reaction of carbinols and hydroperoxides, collectively referred to herein as "organic peroxides." The formation and accumulation of these by-products in the oxidation reaction not only affects the rate of oxidation of DIPB but adversely influences the separation of DHP from the oxidate by the extraction methods carried out later in the process.

The oxidate is then subjected to caustic extraction. The caustic extraction according to the present invention is carried out by using a Karr Column. As will be appreciated by those skilled in the art, a Karr Column is a column having a baffle system of reciprocating plates. A caustic solution, the oxidate and an organic solvent are fed to the Karr Column in a "countercurrent" manner. Suitable organic solvents include, but are not limited to, toluene and m-xylene; preferably, the organic solvent is DIPB. The caustic predominantly removes the DHP while the DIPB or other organic solvent removes the impurities. It is a feature of the present invention, that complete or nearly complete separation of DHP from the DIPB oxidation product and the removal of oxidation impurities from the caustic extract is accomplished by carrying out the caustic extraction and DIPB treatment simultaneously in a single Karr column extractor. When performing the caustic extraction the following conditions in the Karr Column should be monitored: the agitation rate; the temperature; and the feed rates of the oxidate, caustic solution and organic solvent. Agitation should be performed at a rate that allows at least one phase of the solution or mixture to be dispersed. Preferably, an agitation rate of between about 50 and 300 strokes per minute is used, more preferably between about 100 and 150 strokes per minute. If the agitation rate is too fast then flooding will occur in the column resulting in a poor extraction. On the other hand, a slow agitation rate will reduce the mixing between the oxidate and caustic resulting in a poor separation of DHP. The extraction temperature, that is, the temperature of the solution inside the column, is preferably anywhere in the range of about 10 to about 80° C. If the temperature is higher than about 80° C., then dihydroperoxide tends to decompose in the presence of caustic resulting in reduced DHP yield. Column temperatures lower than about 10° C. prevent proper mixing of oxidate and the caustic. For ideal operations, based on extensive extraction testings with the Karr Column, the temperature is preferably kept between 25 and 40° C. Feed rates of the oxidate, caustic, and organic solvent will vary depending on various factors, such as the amount of oxidate being treated and the amount of DHP and HHP present in the oxidate. Optimization of these feed rates can be determined by one skilled in the art based upon the conditions and needs of the user.

It has been found, according to the present invention, that when using this Karr Column operation with the above described extraction conditions, the corresponding dihydroperoxide may be readily and efficiently recovered from the oxidation mixture into the caustic solution. Since the hydroperoxide impurities, such as MHP, MCL, etc., extracted into the caustic extraction are predominantly removed by the organic solvent treatment or backwash, an oxidation recycle carrying these impurities is ready to be fed back into the oxidation reactor. This recycle fraction and a caustic DHP fraction can therefore be simultaneously obtained in a single Karr Column. With this improvement, the oxidation and extraction steps of the hydroperoxidation process can be easily performed in series for the continuous production and extraction of a caustic DHP/HHP stream for use in producing dihydric phenol and dicarbinol by the methods of this invention.

By checking the composition of both the oxidate and the oxidation recycle before and after the caustic extraction, it can be seen that all or nearly all of the KHP and KCL present in the oxidate are extracted into the caustic. These impurities will affect the final DHP purity if not removed. The present invention provides for the removal of these impurities, which are effectively extracted into the cold MIBK extraction described below and, therefore, a very high purity DHP can be obtained.

As stated above, the two streams resulting from the first or caustic extraction Karr Column, include the recycle, which contains impurities, and a caustic DHP fraction, which will also typically contain HHP, KHP and KCL. While the recycle is sent back to the DIPB oxidation reactor, the DHP/HHP caustic fraction is cooled to a temperature between about 10 and 30° C. and fed into a second Karr Column. Preferably, the caustic fraction is fed directly, without delay, into the second Karr Column once the desired temperature is achieved. Cooling is effected to minimize or avoid the decomposition of hydroperoxides, which can be accelerated by elevated temperatures.

While it is preferred to feed the caustic fraction directly or continuously into the second Karr Column, it will be understood that this feeding does not have to be done directly. In order to minimize or avoid the decomposition of hydroperoxides, the caustic solution containing these hydroperoxides should be cooled to as low a temperature as possible if the next extraction is not performed directly after caustic extraction.

In addition to the DHP/HHP rich caustic from the first Karr Column, also fed into the second Karr Column is an organic solvent such as a ketone, preferably methyl isobutyl ketone (MIBK), and a sodium hydroxide solution. The solvent is used to extract the HHP and other impurities, such as KHP, KCL, MHP or other organic peroxides which are known to effect the final DHP purity. The three solutions should be fed to the second Karr Column in a counter-current manner. Two streams are obtained following the cold MIBK extraction: a DHP caustic fraction; and a cold MIBK fraction containing HHP, KHP, KCL, MHP and/or other oxidation by-products. HHP, used for the production of dicarbinol, is therefore obtained directly and continuously from the cold MIBK extraction of the caustic extract using the second Karr Column extraction.

As with the first Karr Column extraction (the caustic extraction), proper conditions should be maintained in the second Karr Column, including temperature, agitation rate and feed rates. The most important condition is the temperature inside the column. For efficient operation, the column temperature, that is, the temperature of the solution inside the column, should be in the range of 10° C. to 30° C., preferably between about 10° C. and 20° C. Because of these temperature ranges, this step is referred to as the cold MIBK extraction step. The term "cold" as used in this context refers to temperatures between about 10° C. and 30° C. If the temperature is much higher than about 30° C., DHP can go into the MIBK layer; temperatures cooler than about 10° C. may make it difficult to perform the operation as precipitation can occur. The agitation rate in the second Karr Column should be such that at least one phase of the solution will be dispersed, and is preferably maintained in a range between about 100 and 400 strokes per minute, more preferably at about 250 strokes per minute. The feed rate of the rich caustic extract, the MIBK or other organic solvent, and the sodium hydroxide solution can be optimized based upon the conditions and needs of the user. Analysis of the cold MIBK extract reveals that all or nearly all of the KHP, KCL, MHP and/or other impurities present in the caustic feed fed to the second Karr Column are completely extracted into the cold MIBK solution.

The caustic extract resulting after the second Karr Column extraction contains almost exclusively DHP, with barely detectable amounts of HHP present in the caustic. The DHP present in the caustic solution is in the form of the disodium salt and can undergo decomposition at elevated temperatures and prolonged storage. As stated above, this caustic extract solution is therefore preferably used directly in the next step to obtain a high purity DHP. As used herein, the term "high purity" when used to describe DHP, means DHP having a purity of 99.7% or higher.

According to the process of the present invention, high purity DHP can be made by subjecting the DHP caustic fraction from the cold MIBK extraction to a second organic solvent extraction, preferably a second MIBK extraction. This second MIBK extraction is a "hot" MIBK extraction, which is performed in a third Karr Column operation. "Hot" as used in this context refers to a temperature of between about 40 and 85° C. The MIBK or other organic solvent is heated to a temperature within this range prior to being fed to the third Karr Column, along with the DHP caustic fraction from the cold MIBK extraction. This "hot" MIBK extraction is preferably carried out in a counter-current manner, where preheated MIBK is preferably passed from the bottom of the column and the caustic solution from the top. In this manner, the DHP salt is not exposed to higher temperature conditions known to cause DHP decomposition. Due to the even temperature gradient inside the column, transformation of DHP salt into DHP can be easily achieved during the extraction.

For efficient column operation, it is preferred to operate the column with the solution inside the column at a temperature of between about 40 and 85° C. By controlling the third Karr Column operating conditions such as temperature, feed rates and agitation rate, a DHP purity of 99.7% can be achieved. It will be appreciated that the higher the purity of the DHP fed into the cleavage step, the higher the purity of the dihydroxybenzene obtained. As stated above, temperatures are preferably maintained between about 40 and 80°

C., more preferably between about 45 and 70° C. The feed rates of MIBK and the caustic solution can be optimized based on the conditions and needs of the user. Agitation rate is such that at least one phase of the solution or mixture will be dispersed, preferably between about 100 and 400 strokes per minute, more preferably about 250 strokes per minute.

The cold and hot extraction steps of the present invention provide a very high purity DHP stream to feed to the cleavage step. Moreover, this very high purity DHP stream is produced in an efficient manner. Both the present methodology and the product obtained are superior to those reported in the art, such as in U.S. Pat. No. 4,059,637. This patent discloses a process in which four mixer-settler extractions are used for the extraction of DHP from a caustic solution previously treated with MIBK to remove the HHP and other impurities. Before the DHP extraction, the DHP content and HHP content of the caustic solution as a material is 11.3 and 0.5%, respectively, and the ratio of DHP:HHP equal to 95.8:4.2. In this multi-stage extraction, a temperature difference between adjacent plates was set up by fixing a heating or cooling device to each plate, for example, by circulating warm water or cold water through the jacket of the extractors. Since each of the four mixer-settlers is an individual operation, the operation of four mixer-settlers requires the use of many pumps, tanks, mixers and motors. In addition, to maintain the temperature of each plate in each mixer-settler, water heating or cooling may be necessary. In spite of the equipment and condition requirements, the final purity of DHP material obtained from this operation is very poor; the DHP and HHP contents in the product are only about 4.83% and 0.38%, respectively in 211 parts MIBK extract, which corresponds to a DHP:HHP ratio of 92.8:7.2. The final ratio is therefore not much higher than the beginning ratio. In contrast, the present invention provides a DHP stream in which the DHP content is 99.7% or higher, using a much less equipment and labor intensive process.

After the hot MIBK extraction, the concentration of DBP in the MIBK is typically between about 6 to 12 wt. % and the amount of water typically between about 1 and 3 wt. %. Preferably, the hot DHP/MIBK solution is concentrated before the cleavage step, as feeding this hot MIBK extraction solution directly into the cleavage reactor often has adverse effects on the resorcinol or hydroquinone yield. Also, it is more economical to use a concentrated DBP solution to maximize the resorcinol or hydroquinone production in the cleavage unit. The hot MIBK solution can be concentrated by any means known in the art. In one preferred method the solution is continuously fed into a vacuum evaporator and concentrated. After the evaporation, the DHP concentration in the solution is typically increased to between about 20 and 40 wt. % and is preferably about 30 wt. %. The water content is typically reduced to about 0.3 wt. %. Though this DHP concentration is suitable for cleavage feed, higher concentrations of DHP may be used if desired. Similarly, while a water content of about 0.3 wt. % does not appear to affect the cleavage rate, this concentration may be lowered by applying more stringent evaporator conditions.

For effecting the acid cleavage of DHP contained in the concentrated MIBK solution, any one of the conventional techniques may be employed. In addition, the cleavage reaction may be carried out by either a continuous or a batchwise process. The reaction may take place within a wide range of temperatures, for example, from between about 30 and 100° C. It has been found convenient to carry out the reaction at the boiling point of the reaction mixture, which is typically in the range of about 60 to 80° C. depending upon the acetone content in the cleavage reactor. By this method, the heat of reaction is dissipated through the reflux. The cleavage of DHP is most conveniently carried out by employing one or more acid catalysts such as sulfuric acid, sulfur trioxide, phosphoric acid, hydrochloric acid, boron trifluoride, p-toluene sulfonic acid, and the like.

The reactor used in the cleavage operation can be comprised, for example, of a stirred reactor or a tubular reactor. Stirred reactors or back mix reactors for carrying out the cleavage reaction are well known. According to the process of the present invention, a continuous cleavage reaction is carried out using a stirred reactor. In this kind of continuous cleavage operation, the reactor is preferably charged with a mixture of either resorcinol or hydroquinone (depending on which dihydroxybenzene is being produced), a sulfur trioxide catalyst dissolved in acetone, and MIBK and raised to the boiling point of the mixture by applied heat. The incorporation of resorcinol or hydroquinone in the starting charge typically improves the cleavage reaction rate. The DHP/MIBK solution and sulfur trioxide dissolved in the acetone are then fed to the reactor at the desired rate and the reaction product is continually removed at about the same rate. In a preferred embodiment, the DHP is fed in the form of a solution in MIBK and sulfur trioxide is fed in an acetone solution. Under these conditions, >99.5% DHP cleavage is possible with a cleavage reactor residence time of between about 5 to 10 minutes.

Once the DHP has been cleaved or rearranged to the corresponding dihydric phenol, the cleavage reaction product should be neutralized to eliminate the acid; the dihydric phenol can then be recovered. The recovery of a polyhydric phenol, such as resorcinol, hydroquinone, etc., from the cleavage reaction mixture by, for example, distillation, extraction and crystallization, are described in the art. According to the process of the present invention, the resorcinol yield from the cleavage reaction is between about 94 and 95% and the purity of resorcinol after distillation is about 99.7% or greater.

Successful and effective separation of DHP and HHP from the caustic solution by the continuous Karr Column cold and hot MIBK extractions gives the HHP raw material for the production of dicarbinol (DCL). DCL is used in the manufacture of various organic and polymeric materials for various applications.

The present invention provides that an aqueous process can be effectively used for the conversion of HHP to DCL. This method takes the HHP obtained from the cold MIBK extraction, and removes MIBK from the reaction mixture. The mixture is then refluxed in an aqueous alkaline solution. Removal of MIBK, previously unreported in the literature, allows an aqueous alkaline solution to be effectively used for the conversion of HHP to DCL. The aqueous alkaline solution is preferably an aqueous sodium hydroxide or an aqueous sodium sulfite solution. Using this methodology, complete HHP decomposition can be achieved in relatively short reaction times, such as 1 to 2 hours.

The aqueous sodium hydroxide and sodium sulfite solutions not only decomposed the HHP to DCL but also are believed to decompose the other hydroperoxides, namely KHP and MHP, into their corresponding carbinols (KCL and MCL) although the inventors do not wish to be bound by this. In the case of sodium sulfite decomposition, according to the process of the present invention, the conversion of HHP to DCL can be achieved even in the presence of MIBK solvent. After the decomposition, DCL product is then easily filtered and purified for commercial markets. The process of the present invention therefore provides an improved and safe aqueous process for the manufacture of DCL from HHP material.

The organic solvent used in the "cold" and "hot" extractions in the second and third Karr Columns can be recycled and reused. This organic solvent, which is preferably MIBK, can be recovered from the HHP stream generated during the cold MIBK extraction prior to the decomposition step. MIBK can be recovered, for example, through distillation of the HHP stream. Similarly, residual MIBK in the lean caustic can be recovered through distillation of the lean caustic stream generated during the "hot" extraction in the third Karr Column. The MIBK, or other organic solvent, recovered can then be recycled to the second and third Karr Column extraction steps. This recycle further contributes to the economy and efficiency of the present methods.

It will be appreciated that the present invention provides a means for the preparation of DHP and HHP using Karr Columns. These Karr reciprocating plate columns have several advantages over known methods for obtaining a pure DHP fraction, namely: high efficiency and high capacity (high volumetric efficiency) are achieved in a single compact unit; and elimination of the many pumps, mixers and motors required, for example, by mixer-settler operations. Only a single Karr Column is required for each of the three extraction steps, as opposed to the multiple mixers and settlers required in methodologies reported in the art. The ability to easily reverse phases during extraction is another advantage of the present methods. Experimental work demonstrated that when the DHP enriched aqueous phase was dispersed in both the "cold" and "hot" MIBK Karr Columns, coalescence at the interface was good and entailment of the solvents was negligible.

In the single Karr Column operations of the present invention, the temperature of the aqueous alkali layer gradually increases as the layer is passed in a counter current means through the plates. Therefore, the Karr Column operation avoids a large or uneven temperature difference between the adjacent plates and a smooth temperature gradient can be achieved from the bottom to the top of the column.

Preferably, the three Karr Columns used in the present methods are connected and run in series. Thus, the present invention provides an advantage over the art in that any or all of the steps described herein can be performed in a continuous manner, with the product from one column being sent directly, or without appreciable delay, to the next column. The ability to run such an efficient, continuous method has not been previously reported in the art.

The Karr reciprocating plate extraction columns as used in the present invention can be obtained from KOCH Process Technology, 1055 Parsippany Blvd., Parsippany, N.J. 07054.

NMR spectroscopy was used to characterize the oxidation products of the staring DIPB solution by the proton magnetic resonance (PMR) method. The present invention is therefore also directed to a method of using PMR to determine the composition of the various streams generated by the methods of the present invention. In addition to crude oxidation product (oxidate), PMR methods were developed to characterize the recycle product, cold and hot MIBK extraction products, cleavage feed and cleavage product, and the product obtained at different stages of distillation in the recovery of high purity resorcinol. Use of the PMR technique allowed for characterization of all the components of the DIPB hydroperoxidation process including organic peroxides, which were previously unidentified. This characterization was previously unreported in the art.

For qualitative characterization of the various streams described above, a PMR analysis was performed. The PMR analysis according to the present invention uses the five most common organic moieties produced from DIPB oxidation in order to identify the compounds present in each stream; these organic structures are:

The portion of the structure shown in bold type represent the hydrogens (protons) that were actually used to determine the structures present in each stream or product. PMR spectra for the oxidate, recycle streams, cold and hot MIBK extraction streams were obtained. Identification of each peak of each spectra was determined by comparing peak locations with those obtained using standards for each component of the streams.

To determine the molar ratio of the components in each stream or product, the integral value for the structure being measured was determined. By measuring the height of the integral for each peak, and dividing the height by the number of protons giving rise to that integral, the mole fraction of each compound is determined. The number of protons giving rise to the integral or peak will be either 3, 6 or 12, as shown in the above organic structure formulas and as would be known to those skilled in the art. The organic composition of these streams is then found by a "Weight Ratio" method whereby the weight fraction of each component is determined, and the total normalized to equal 100. Typically, the weight ratio will be very close to weight percent values, so long as the sample is not high in water, inorganic material, or compounds that do not contain hydrogen.

PMR methods for analyzing the cleavage product and distillation samples differed, as there are unassigned or unknown compounds in these products that cannot be measured or compared against known standards. An "Internal Standard/PMR" method can be used for analyzing these streams, in which a weighted portion of sample is "spiked" with a known amount of an organic compound or "internal standard". Any organic compound can be used, provided problems with compatibility do not arise. Preferred for this use is methylene chloride, which is compatible with the products and which yields only 1 peak in the spectrum. When using methylene chloride, between about 20 and 30 mg per 100 mg of sample should be used. The weight of each analyte is then found according to the following formula:

weight of analyte=(weight organic compound) $(N_s/N_a)(M_a/M_s)(A_a/A_s)$ where
$N_s$=number of protons from internal standard (2 for methylene chloride)
$N_a$=number of protons from analyte for the structure measured
$M_s$=molecular weight of standard (85 for methylene chloride)

$M_a$=molecular weight of analyte
$A_s$=integral area of standard
$A_a$=integral area of analyte The weight of the analyte is divided by the weight of the sample to give the weight percent of each analyte in the total composition.

Prior to performing PMR analysis on the DHP/HHP and DHP rich caustic streams from the caustic extraction Karr Column and the Cold MIBK Extraction Karr Column, the streams should be subjected to an extraction to remove the NaOH. Extraction is performed by using an organic solvent, such as benzene. For example, a known amount of the stream should be treated with dry ice to bring the stream to a pH within the range of about 9 and 9.5, and extracted with benzene. The sample can be tested then, or can be further treated by distilling off the benzene and the remaining residue analyzed by the PMR methods. Other streams and products can be analyzed directly.

The 200 MHz PMR spectra can be acquired, for example, on a Varian Gemini 200 FT-NMR spectrometer, commercially available from Varian Associates, Palo Alto, Calif., by preparing a 3 to 5% (by weight) of the unknown in acetone-d6 (($CD_3)_2C=O$). Typical acquisition parameters are as follows: pulse width=8 microseconds (a 30 degree pulse); pulse delay=3 seconds; acquisition time=4 seconds; and number of transients=100. The spectra are "split" into sections 0.3 ppm (60 Hz) wide with full integration for each and accuracy of measurement. Parameters other than these can be optimized based on the needs and apparatus of the user. It will be appreciated that spectra can be obtained at MHz greater than 200, depending on the needs and equipment of the user. Spectra obtained using less than 200 MHz will typically have inadequate resolution.

The PMR method of analysis offers advantages over other analytical techniques for the analysis of hydroperoxidation materials, namely: the technique is nondestructive; all samples are analyzed in deuterated solvents which provide an internal reference to ensure correct chemical shift values; the technique is based on measurement of integrals arising from the different proton types present in the mixture—since all protons organically bound to a carbon atom will "respond" in an equivalent manner, there is no need to determine a "response factor" for each compound; all components are measured from a single spectrum (changes in instrument conditions will not affect the analysis); once the chemical shift values for a standard have been determined, there is no need to concurrently analyze the standard during analysis of unknown mixtures; and the analysis is fast, typically requiring 15 minutes or less of instrument time.

Figure 1:
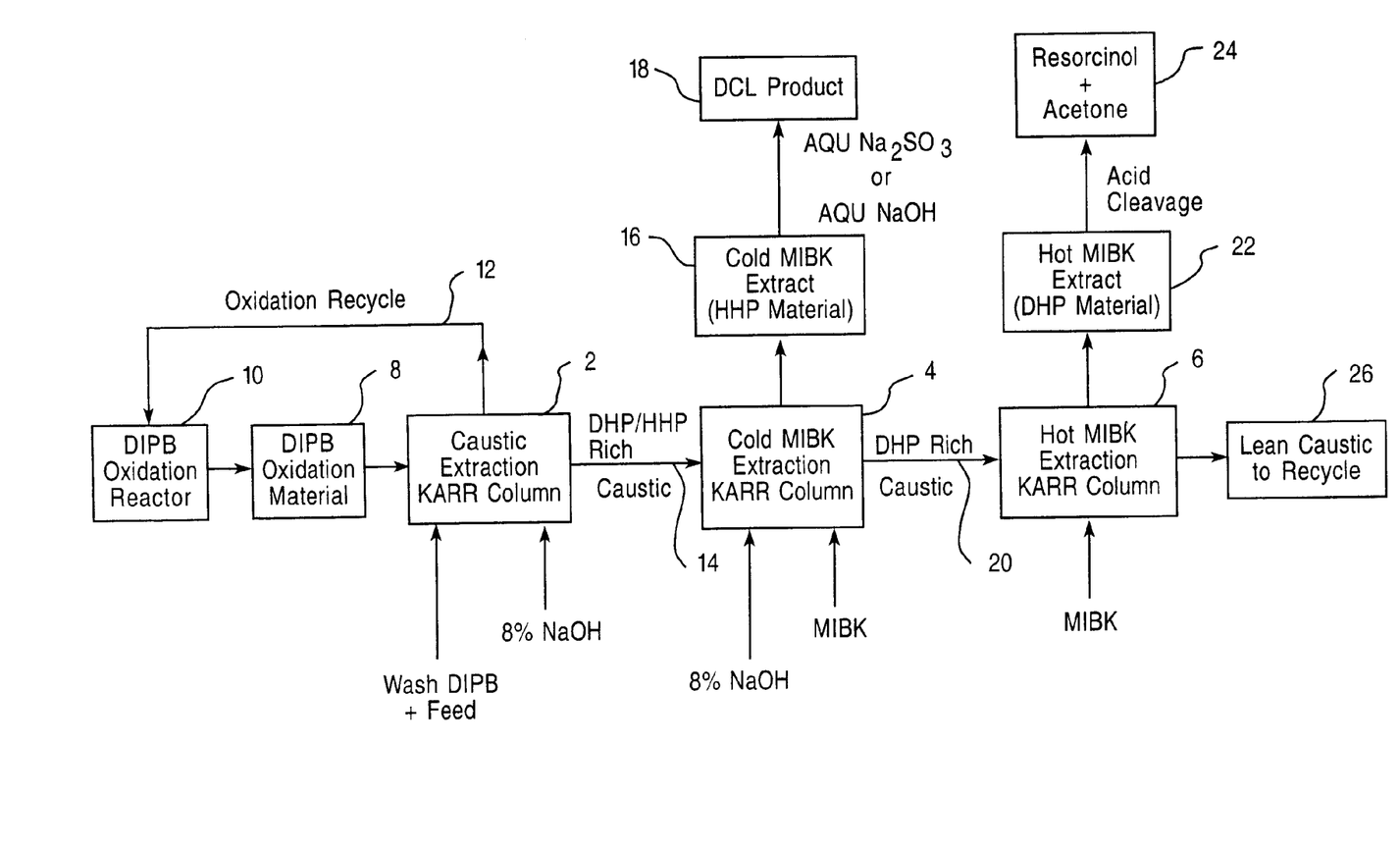
FIG. 1 is a schematic flow diagram for a preferred embodiment of the process for producing dihydric phenol and dicarbinol from diisopropylbenzene according to the present invention.

As an aid in understanding the process of the present invention, the simultaneous extraction of DHP and HHP from the oxidate and their subsequent separations by the cold and hot MIBK extractions using Karr Columns operations are described with reference to the schematic flow diagram illustrated in FIG. 1, with the understanding that this is an exemplary embodiment of the present invention. Referring to FIG. 1, three Karr Columns are connected in a series and are referred to as Caustic Extraction Karr Column 2, Cold MIBK Extraction Karr Column 4 and Hot MIBK Extraction Karr Column 6. The DIPB oxidation material 8 or oxidate coming from the DIPB Oxidation Reactor 10, wash DIPB and 8% aqueous sodium hydroxide are fed to the Caustic Extraction Karr Column 2 in such a way that DIPB and caustic solution flow countercurrently in the caustic extraction column. The organic recycle ("oxidation recycle") 12 collected from the column will be directly returned to the DIPB Oxidation Reactor 10 for further oxidation. The aqueous caustic solution enriched with DHP and HHP ("DHP/HHP rich caustic") 14 separated by the Caustic Extraction Karr Column 2 is sent to the Cold MIBK Extraction Karr Column 4 after being cooled through a cooler (not shown). In the Cold MIBK Extraction Karr Column 4, the DHP/HHP rich caustic 14, an MIBK solvent and 8% sodium hydroxide solution are introduced in such a way that both MIBK and wash caustic are passing each other countercurrently in the column. From this column, the MIBK solution containing HHP is recovered ("Cold MIBK Extract") 16 and the HHP converted into DCL 18 by use of an aqueous sodium sulfite or sodium hydroxide solution; during this conversion, the solvent MIBK is also recovered for recycle (not shown). The aqueous caustic extract enriched with DHP ("DHP Rich Caustic") 20 is separated from the Cold MIBK Extraction Karr Column 4 and is pumped directly to the Hot MIBK Extraction Karr column 6. In this column, the DHP Rich Caustic 20 and previously heated MIBK are pumped in such a way that both caustic solution and MIBK solvent are countercurrently passing each other. The Hot MIBK Extract 22 obtained from this extraction contains DHP with a purity in excess of 99.7%. The HHP impurity present in this DHP material is typically 0.3%; the weight ratio of DHP/HHP in the MIBK extract is therefore about 99.7:0.3. The Hot MIBK Extract 22 is subsequently concentrated (not shown) and cleaved in the presence of an acid catalyst to produce the dihydric phenol, such as resorcinol, and acetone 24. The lean caustic 26 collected from the Hot MIBK Extraction Karr Column 6 can be recycled after stripping off the dissolved MIBK.

EXAMPLES

The present invention is further described in more detail by way of the following Examples. The Examples provided below should not be taken as restrictive of the scope of the invention. All parts, percentages and ratios are by weight.

Example 1

Preparation of Diisopropylbenzene Oxidation Mixture

Three hundred parts of m-diisopropylbenzene (m-DIPB) were mixed with 30 parts of m-diisopropylbenzene monohydroperoxide (MHP; initiator) and 10 parts of 4% aqueous sodium hydroxide (catalyst) in a 1 liter Parr reactor and oxidized by passing air at the rate of 20 liters/hour with good agitation. The temperature of the oxidation reaction mixture was maintained at about 90° C. The oxidation was continued until the product contained 70 to 75% hydroperoxide (determined by the iodimetric titration and calculated as diisopropylbenzene monohydroperoxide). NMR analysis of this oxidation material (oxidate) showed the presence of about 15–18% m-diisopropylbenzene dihydroperoxide (DHP) and 3 to 5% m-diisopropylbenzene hydroxyhydroperoxide (HHP) in addition to the oxidation by-products shown in Table 1, below, and unreacted DIPB.

Continuous and Simultaneous Separation of DHP and HHP from m-DIPB Oxidation Product The oxidate obtained from the m-DIPB oxidation was cooled to room temperature and pumped into a Karr Column (Caustic Extraction Column) at a rate of 100 parts/hour. Separately, m-diisopropylbenzene and 8% aqueous sodium hydroxide were pumped into the column at the rate of 13.5 parts/hour and 88.8 parts/hour, respectively, in such a way that both the liquids passed countercurrently in the column.

During this operation, the column temperature was maintained between 25 to 40° C. and two phases, namely organic and aqueous, were separated continuously. The organic phase was collected at the rate of 91.8 parts/hour, and contained most of the monohydroperoxide (MHP) as well as oxidation products unextracted by the caustic solution. This recyclable organic phase can be effectively returned to the oxidizer for the continuous or batch oxidation. The aqueous phase (rich caustic extract) enriched with DHP, HHP, KHP and other caustic extractable impurities was collected at the rate of 110.5 parts/hour.

The rich caustic extract obtained from the first Karr Column (caustic extraction) was cooled and pumped into the second Karr Column (cold MIBK column) at a rate of 110.5 parts/hour; the column temperature of the second column was maintained between about 10 to 30° C. temperature during the extraction. The methyl isobutyl ketone and 8% aqueous sodium hydroxide solutions were respectively pumped into the column at the rate of 58.5 parts/hour and 51.0 parts/hour. When these two solutions were passing countercurrently in the column, the HHP, KHP and all the oxidation impurities present in the caustic were extracted into the organic phase. The HHP enriched organic phase (cold MIBK extract) was collected at the rate of 63.5 parts/hour. The aqueous caustic extract separated from this Karr Column operation was found to contain 99.8% DHP.

Without any isolation or recovery, the DHP rich caustic extract obtained from the cold MIBK column was directly pumped into a third Karr Column (hot MIBK column). Separately, previously heated methyl isobutyl ketone solvent was pumped into this column at a rate of 134.5 parts/hour in such a way that this solvent countercurrently passed the caustic solution. A uniform temperature gradient was maintained throughout the column such that the column temperature was between about 30 and 70° C. The DHP present in the caustic was efficiently extracted with minimal decomposition and the MIBK extract (hot MIBK extract) was collecting at a rate of 151.5 parts/hour. The purity of DHP obtained from this extract was determined to be 99.7%. The aqueous caustic (lean caustic) recovered at the rate of 139.5 parts/hour from this column can be recycled back to the caustic extraction column after the removal of entrained MIBK.

Table 1 summarizes the compositions of different streams according to the methods of Example 1.

TABLE 1

Extraction and Simultaneous Separation of DHP and HHP from DIPB Oxidation Mixture Using Karr Columns
Composition of Different Streams
NMR Analysis Results (weight ratios)

| Component | m-DIPB Oxidation Material | Oxidation Recycle | Cold MIBK Extract (MIBK Solvent Free) | Hot MIBK Extract (MIBK Solvent Free) |
|---|---|---|---|---|
| 1. DIPB | 26.6 | 43.4 | | |
| 2. MHP | 38.8 | 44.9 | 7.2 | |
| 3. DHP | 18.2 | 0 | 1.1 | 99.7 |
| 4. HHP | 4.3 | 2.2 | 77.8 | 0.3 |
| 5. MCL | 3.5 | 5.4 | | |
| 6. DCL | 0.6 | 0.6 | 0.7 | |
| 7. MKT | 0.4 | 0.1 | | |
| 8. KHP | 1.0 | 0 | 12.5 | |
| 9. KCL | 0.2 | 0 | 0.7 | |
| 10. Organic Peroxides | 6.0 | 3.4 | — | — |

The hot MIBK extract obtained from the third Karr Column was concentrated to 30 wt. % DHP. During this concentration, the water content of the DHP/MIBK solution was reduced from 3.0 wt. % to 0.3 wt. %. This material was used in the following continuous cleavage operation.

Continuous Cleavage of DHP Material

Into a glass reactor fitted with a mechanical stirrer, thermometer, reflux condenser and an overflow arrangement, a solution containing resorcinol, methyl isobutyl ketone and 0.06 parts by weight of $SO_3$ dissolved in acetone solution at the weight ratio of 8:52:40 was charged and heated to reflux. Solutions containing 30% weight/weight of DHP in methyl isobutyl ketone (solution from the hot MIBK extract) and 0.06% weight/weight of sulfur trioxide in dry acetone were fed into the reactor at a rate of 50.0 parts/hour and 26.9 parts/hour, respectively, in such a way that the total residence time was 10 minutes. The temperature of the cleavage reactor contents was maintained at the boiling point. The cleavage product from the reactor overflowed into a collector in which the acid catalyst was immediately and continuously neutralized. The product collected, after the steady state conditions, gave a 94% yield of resorcinol based on the DHP feed.

Manufacture of DCL from HHP (Sodium Sulfite Decomposition with Azeotropic Distillation Method)

The cold MIBK extract obtained from the second Karr Column was concentrated to about 40 wt. % HHP material in the MIBK. By doing this operation, most of the MIBK solvent can be effectively recovered and recycled.

The reactor, equipped with a mechanical stirrer, thermometer and Dean-Stark condenser, was charged with 100 parts of 40% HHP in methyl isobutyl ketone (cold MIBK extract containing 77.8% HHP) and 140 parts of 20% aqueous sodium sulfite solution. The contents of the reactor were heated to reflux and all the solvent MIBK present in the reactor was completely removed by azeotropic distillation. After the solvent removal, the contents of the reactor were refluxed for a period of 2.0 hours and cooled to precipitate the DCL. The white precipitate separated from the aqueous solution was filtered, washed with water and then dried. The yield was 26.7 parts with a purity of 94.2%. From the results of this experiment, all the HHP present in the cold MIBK extract was completely decomposed to DCL.

From this example, it is evident that both resorcinol and dicarbinol can be simultaneously produced from diisopropylbenzene.

Example 2

In this example, the two methods developed for the decomposition of HHP to DCL by the aqueous sodium sulfite solution are disclosed.

A cold MIBK extract obtained from the Karr Column was concentrated to about 40 wt. % of HHP material and used in the following two experiments:

Decomposition of HHP to DCL by Aqueous Sodium Sulfite

A. Azotrope Method

Into a three necked flask fitted with a mechanical stirrer, thermometer and Dean-Stark condenser, 100 parts of HHP/MIBK and 140 parts of 20% aqueous sodium sulfite solution were added. Then, the contents of the flask were heated and taken to reflux. During this reflux period, by means of Dean-Stark separation, all the MIBK solvent present in the solution was removed. After this, the contents of the flask were refluxed for an addition period of 2.0 hours and then cooled. The solid material separated on cooling was filtered, washed with water, dried and analyzed for its composition by NMR analysis. The yield was 28.4 parts with 94.2% purity. Results are summarized in Table 2, below.

B. Reflux Method

Into a three necked flask fitted with a mechanical stirrer, thermometer and reflux condenser, 100 parts of concentrated HHP/MIBK solution and 140 parts of 20% aqueous sodium sulfite were added. The contents of the flask were heated and taken to reflux for 2.0 hours. After this reflux, the reaction mixture was cooled and the white precipitate separated was filtered, washed with water, dried and analyzed by NMR for its composition. The yield was 21.6 parts and purity was 97.6%. Results of this experiment are summarized in Table 2.

TABLE 2

Decomposition of HHP to DCL Using Aqueous $Na_2SO_3$ Solution

| Method | Control* | Azeotrope | Reflux |
|---|---|---|---|
| Materials Used (parts) | | | |
| 1. HHP/MIBK Solution | | 100 | 100 |
| 2. $Na_2SO_3$ Solution (20 wt. %) | | 140 | 140 |
| Conditions | | | |
| 1. Reflux Temperature (° C.) | | 101 | 95–100 |
| 2. Reflux Time (hours) | | 2 | 2.0 |
| NMR Analysis of Organic Phase | | | |
| Components (wt. ratio, solvent free) | | | |
| 1. DHP | 0.0 | 0 | 0 |
| 2. HHP | 77.9 | 0 | 0 |
| 3. KHP | 10.6 | 0 | 0 |
| 4. MHP | 9.6 | 0 | 0 |
| 5. KCL | 0.9 | 5.8 | 1.9 |
| 6. DCL | 0.7 | 94.2 | 97.6 |
| 7. MCL | 0 | 0 | 0.4 |
| MIBK (wt. %) | 61.0 | 0 | 0.1 |

*Cold MIBK Extract was concentrated to about 39 wt. % solids and used in the Decomposition Process.

On analyzing the Table 2 results, it is seen that decomposition of HHP using an aqueous sodium sulfite solution can be successfully used for the safe and efficient conversion of HHP to DCL. By this method, it was observed that the HHP material was completely converted into its corresponding carbinol under atmospheric conditions. With this method, even before the purification, the DCL obtained was of high purity.

Example 3

In this example, processes for making DCL directly from the cold MIBK extract using aqueous sodium hydroxide solution are disclosed.

Experiment No. 1

Into a three necked flask fitted with a mechanical stirrer, thermometer and reflux condenser, 100 parts of cold MIBK extract, obtained from the Karr Column operation, and 24 parts of 4% aqueous caustic solution were added and refluxed for a period of 5.0 hours. After this reflux period, the solution was cooled, and both the aqueous and organic layers were separated, and the organic layer analyzed for its composition by NMR analysis. On analyzing the results, it was observed that the concentration of HHP in the MIBK layer remained unaffected indicating no decomposition of HHP was taking place under the above conditions.

Experiment No. 2

Experiment No. 1 was repeated using 8% aqueous sodium hydroxide solution was used in the place of 4% aqueous sodium hydroxide solution. The separated MIBK phase after the reflux period was analyzed by NMR for its composition. Again, no change in the HHP concentration was seen. Results obtained from Experiments 1 and 2 are summarized in Table 3, below.

On investigating this further, it was discovered that the decomposition of HHP could be effectively completed by removing MIBK from the reaction mixture before refluxing. With this discovery, a method was developed for effectively decomposing HHP to DCL. Therefore, by using the method described in Experiment No. 3, DCL could be manufactured in a safe and an economical manner. The advantages of this method are that it is aqueous, performed under atmospheric rather than nonhigh pressure conditions, and performed without the use of hydrogen.

TABLE 3

Decomposition of HHP to DCL Using Aqueous NaOH (Reflux of HHP/MIBK with NaOH Solution)

| Experiment | Control | No. 1 | No. 2 |
|---|---|---|---|
| Materials Used (parts) | | | |
| 1. HHP/MIBK Solution | | 100 | 100 |
| 2. NaOH Solution (wt. %) | | 24 (4%) | 24 (8%) |
| Conditions | | | |
| 1. Reflux Temperature (° C.) | | 90–95 | 90–95 |
| 2. Reflux Time (hours) | | 5.0 | 5.5 |
| NMR Analysis of Organic Phase | | | |
| Components (wt. ratio, solvent free) | | | |
| 1. DHP | 14.7 | 8.5 | 3.5 |
| 2. HHP | 66.8 | 66.2 | 69.4 |
| 3. KEP | 7.7 | 8.8 | 8.1 |
| 4. KCL | 0.9 | 2.4 | 3.0 |
| 5. DCL | 2.2 | 5.7 | 7.3 |
| 6. MHP | 7.7 | 8.4 | 7.9 |
| 7. DKT | — | — | 0.8 |
| 8. MIBK Solvent (wt. %) | 95.4 | 95.7 | 95.7 |

*HHP/MIBK solution used in the Decomposition Process

Experiment No. 3

Into a three necked flask fitted with a mechanical stirrer, thermometer and Dean-Stark condenser 100 parts of concentrated HHP/MIBK and 44.4 parts of 20% aqueous sodium hydroxide were added. The contents of the flask were heated and refluxed. During this initial reflux period, all the MIBK solvent was completely removed as an azeotrope. After this, the reactor contents were refluxed for an additional period of 1.0 hour. Then the solution was cooled and the white precipitate separated was filtered, washed with distilled water, dried and analyzed by NMR for its composition. The yield was 26.4 parts with a purity of 94.6%. The results of this experiment are summarized in Table 4 and clearly suggest that an aqueous sodium hydroxide solution can also be effectively used for the complete decomposition of HHP.

TABLE 4

Decomposition of HHP to DCL Using Aqueous NaOH Solution
(Dean-Stark Distillation of MIBK)

| Method | Control* |
|---|---|
| Materials Used (g) | |
| 1. HHP/MIBK Solution | 100.0 |
| 2. NaOH Solution (20 wt. %) | 44.4 |
| Conditions | |
| 1. Reflux Temperature (° C.) | 95–105 |
| 2. Reflux Time (hours) | 1 |
| NMR Analysis of Organic Phase | |
| Components (wt. ratio, solvent free) | |
| 1. DHP | 0.0 |
| 2. HHP | 77.9 |
| 3. KHP | 10.6 |
| 4. MHP | 9.6 |
| 5. KCL | 0.9 |
| 6. DCL | 0.7 |
| 7. DKT | 0 |
| 8. MCL | 0 |
| 9. MKT | 0 |
| 10. MIBK (wt. %) | 61.0 |

| | |
|---|---|
| | 0 |
| | 0 |
| | 0 |
| | 0 |
| | 2.6 |
| | 94.6 |
| | 0 |
| | 2.8 |
| | 0 |
| | 0 |

*Cold MIBK Extract was concentrated to about 30 wt. % solids and used in the Decomposition Process.

Example 4

Preparation of Diisopropylbenzene Oxidation Mixture

A Parr reactor was charged with 100 parts of m-diisopropylbenzene (m-DIPB), 10 parts of oxidation recycle (initiator) and 2 parts of 5% sodium carbonate (catalyst) solution. The above mixture was heated to 95° C. and oxidized by passing a fine stream of air into the rapidly stirred solution. The oxidation was continued until the oxidation mixture in the reactor contained 75 wt. % hydroperoxide (calculated as diisopropylbenzene monohydroperoxide by iodimetric titration). The analysis result of this m-DIPB oxidation material (oxidate) is given in Table 5, below.

Continuous and Simultaneous Separation of DHP and HHP from m-DIPB Oxidation Product The oxidate obtained from the m-DIPB oxidation was cooled to room temperature and pumped into a Karr Column (Caustic Extraction Column) at a rate of 100 parts/hour. Separately, m-diisopropylbenzene and 8% aqueous sodium hydroxide were pumped into the column at the rate of 12.9 parts/hour and 73.6 parts/hour, respectively, in such a way that both the liquids passed countercurrently in the column. During this operation, the column temperature was maintained between 25 to 40° C. and two phases, namely organic and aqueous, were separated continuously. The organic phase was collected at the rate of 93.5 parts/hour, and contained most of the monohydroperoxide (MHP) as well as oxidation products unextractable by the caustic solution. This recyclable organic phase can be effectively returned to the oxidizer for the continuous or batch oxidation. The aqueous phase (rich caustic extract) enriched with DHP, HHP, KHP and other caustic extractable impurities shown in Table 5 were collected at the rate of 91.0 parts/hour.

The rich caustic extract obtained from the first Karr Column was cooled and pumped into the second Karr Column (cold MIBK column) at a rate of 91.0 parts/hour; this second column temperature was maintained between about 10 to 30° C. temperature during the extraction. The methyl isobutyl ketone and 8% aqueous sodium hydroxide solutions were respectively pumped into the column at the rate of 63.4 parts/hour and 52.0 parts/hour. When these two solutions were passing countercurrently in the column, the HHP, KHP and all the oxidation impurities present in the caustic were extracted into the organic phase. The HHP enriched organic phase (cold MIBK extract) was collecting at the rate of 68.6 parts/hour. The aqueous caustic extract separated from this Karr Column operation was found to contain 99.8% DHP.

Without any isolation or recovery, the DHP rich caustic extract obtained from the cold MIBK column was directly pumped into a third Karr Column (hot MIBK column). Separately, previously heated methyl isobutyl ketone solvent was pumped into this column at a rate of 138.0 parts/hour in such a way that this solvent countercurrently passed the caustic solution. A uniform temperature gradient was maintained throughout the column such that the column temperature was between about 30 and 70° C. The DHP present in the caustic was efficiently extracted with minimal decomposition and the MIBK extract (hot MIBK extract) was collected at a rate of 150.0 parts/hour. The purity of DHP obtained from this extract was determined to be 99.7%. The aqueous caustic (lean caustic) recovered at the rate of 127.6 parts/hour from this column can be recycled back to the caustic extraction column after the removal of entrained MIBK.

Table 5 summarizes the results of the above experiment.

TABLE 5

Extraction and Simultaneous Separation of DHP and HHP from DIPB
Oxidation Mixture Using Karr Columns
Composition of Different Streams
NMR Analysis Results (weight ratios)

| Component | m-DIPB Oxidation Material | Oxidation Recycle | Cold MIBK Extract (MIBK Solvent Free) | Hot MIBK Extract (MIBK Solvent Free) |
|---|---|---|---|---|
| 1. DIPB | 24.9 | 44.0 | | |
| 2. MHP | 38.2 | 42.7 | 8.7 | |
| 3. DHP | 18.7 | 0 | 1.4 | 99.7 |
| 4. HHP | 4.3 | 2.7 | 76.2 | 0.3 |
| 5. MCL | 4.0 | 6.1 | | |
| 6. DCL | 0.6 | 0.8 | 0.4 | |
| 7. MKT | 0.4 | 0.1 | | |
| 8. KHP | 1.0 | 0 | 12.4 | |
| 9. KCL | 0.2 | 0 | 0.9 | |
| 10. Organic Peroxides | 5.9 | 3.6 | — | — |

The hot MIBK extract obtained from the third Karr Column was concentrated to 24.8 wt. % DHP. During this concentration, the water content of the DHP/MIBK solution was reduced from 3.0 wt. % to 0.3 wt. %. This material was used in the following continuous cleavage operation.

Continuous Cleavage of DHP Material

Into a glass reactor fitted with a mechanical stirrer, thermometer, reflux condenser and an overflow arrangement, a solution containing resorcinol, methyl isobutyl ketone and 0.06 parts by weight of $SO_3$ dissolved in acetone solution at the weight ratio of 8:52:40 was charged and heated to reflux. Solutions containing 24.8% weight/weight of DHP in methyl isobutyl ketone (solution from the hot MIBK extract) and 0.06% weight/weight of sulfur trioxide in dry acetone were fed into the reactor at a rate of 100.0 parts/hour and 53.8 parts/hour, respectively, in such a way that the total residence time was about 5 minutes. The temperature of the cleavage reactor contents was maintained at the boiling point. The cleavage product from the reactor overflowed into a collector in which the acid catalyst was immediately and continuously neutralized. The product collected, after the steady state conditions, gave a 91% yield of resorcinol based on the DHP feed.

Manufacture of DCL from HHP (Sodium Hydroxide Decomposition with Azeotropic Distillation Method)

The cold MIBK extract obtained from the second Karr Column was concentrated to obtain 40 wt. % HHP material in the MIBK. By doing this operation, most of the MIBK solvent can be effectively recovered and recycled.

A reactor equipped with a mechanical stirrer, thermometer and Dean-Stark condenser was charged with 100 parts of 40% HHP in methyl isobutyl ketone (cold MIBK extract containing 76.2% HHP) and 44.4 parts of 20% aqueous sodium hydroxide solution. The contents of the reactor were heated to reflux and all the solvent MIBK present in the reactor was completely removed by azeotropic distillation. After the solvent removal, the contents of the reactor were refluxed for a period of about 1.0 hour and cooled to precipitate the DCL. The white precipitate separated from the aqueous solution was filtered, washed with water and then dried. The yield was 26.2 parts with a purity of 97.1%. From the results of this experiment, it was determined that all the HHP present in the cold MIBK extract was completely decomposed.

From this example, it is evident that both resorcinol and dicarbinol can be produced from diisopropylbenzene.

Example 5

A Parr reactor charged with 330.0 parts of p-diisopropylbenzene, 10.0 parts of oxidation recycle and 9.0 parts of 4% aqueous sodium hydroxide and was heated to 95° C. The oxidation of the above mixture was started by passing a fine stream of air at a rate of 20 liters/hour into rapidly stirred solution. The oxidation reaction took about 14.0 hours to reach 75% hydroperoxide content calculated as p-diisopropylbenzene monohydroperoxide by iodimetric titration. This p-DIPB oxidation material could also be used to make the corresponding dihydric phenol, namely hydroquinone, and dicarbinol by the process of this invention.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for manufacturing dihydroxybenzene and dicarbinol from diisopropylbenzene comprising:
   a) oxidizing diisopropylbenzene (DIPB) in the presence of a base catalyst to obtain an oxidate comprising diisopropylbenzene dihydroperoxide (DHP), diisopropylbenzene hydroxyhydroperoxide (HHP), acetyl-isopropylbenzene hydroperoxide (KHP), and one or more members selected from the group consisting of diisopropylbenzene monohydroperoxide (MHP), isopropylbenzene monocarbinol (MCL), diisopropylbenzene dicarbinol (DCL), acetyl-isopropylbenzene monocarbinol (KCL) and other organic peroxides;
   b) feeding the oxidate of step a), a caustic solution and an organic solvent into a first reciprocating plate counter-current extraction column;
   c) generating two streams from the first reciprocating plate counter-current extraction column of step b), the first caustic extraction stream comprising DHP, HHP and KHP extracted in a countercurrent operation, and the second caustic extraction stream comprising one or more members selected from the group consisting of MHP, MCL, DCL, KCL, other organic peroxides, DIPB and the organic solvent of step b);
   d) feeding the first caustic extraction stream from step c) cooled to a temperature of between about 10 and 30° C., an organic solvent and an alkaline solution into a second reciprocating plate counter-current extraction column;
   e) generating two streams from the second reciprocating plate counter-current extraction column, the first cold extraction stream comprising a cold organic solvent extract comprising HHP and KHP and the second cold extraction stream comprising DHP enriched caustic;
   f) feeding an organic solvent having a temperature of between about 40 and 85° C. and the DHP enriched caustic of step e) into a third reciprocating plate counter-current extraction column;
   g) generating two streams from the third reciprocating plate counter-current extraction column, the first hot extraction stream comprising a hot organic solvent solution comprising high purity DHP, and the second hot extraction stream comprising lean caustic having low levels of unextracted hydroperoxides;
   h) concentrating the hot organic solvent solution of step g) and feeding the concentrate into a continuous cleavage reactor where DHP is cleaved in the presence of an acid catalyst to produce a solution comprising the corresponding dihydroxybenzene and acetone; and
   i) decomposing the HHP present in the first cold extraction stream of step e) by treatment with an aqueous alkaline solution under atmospheric pressure and aqueous conditions to obtain the corresponding dicarbinol.

2. The method of claim 1, wherein at least two successive steps selected from the group consisting of any of steps a) through g) are performed continuously.

3. The method of claim 1, wherein the oxidation of diisopropylbenzene is performed using molecular oxygen.

4. The method of claim 3, wherein the oxidation step is performed using either a continuous or a batchwise method.

5. The method of claim 1, including performing said oxidation step at a temperature between about 80 and 120° C. and a pressure of between about 20 and 80 psi and using as the base catalyst an alkaline solution selected from the group consisting of sodium carbonate and sodium hydroxide.

6. The method of claim 1, wherein the organic solvent of step b) is DIPB.

7. The method of claim 1, further including the step of recycling the second caustic extraction stream produced in step c) to the oxidation step of step a).

8. The method of claim 1, wherein the organic solvent used in step d) and step f) is methyl isobutyl ketone.

9. The method of claim 1, wherein the temperature of the solution inside the second reciprocating plate counter-current extraction column is between about 10 and 30° C.

10. The method of claim 1, wherein the temperature of the solution in the third reciprocating plate counter-current extraction column is between about 40 and 85° C.

11. The method of claim 1, wherein the first caustic extraction stream of step c) is fed directly to the cold extraction of step d), and wherein the second cold extraction stream of step e) is fed directly to the hot extraction of step f).

12. The method of claim 1, including effecting the concentration of step h) by feeding the hot organic solvent solution into a vacuum evaporator.

13. The method of claim 1, wherein the temperature of the solution inside the cleavage reactor in step h) is between about 60 to 80° C.

14. The method of claim 13, wherein the decomposition step i) is performed at a temperature between about 90 and 105° C.

15. The method of claim 1, wherein said first reciprocating plate counter-current extraction column, said second reciprocating plate counter-current extraction column and said third reciprocating plate counter-current extraction column are operated in series.

16. The method of claim 1, including employing said method to produce a hot organic solvent solution having a DHP purity of about 99.7% or greater.

17. The method of claim 1, wherein the aqueous alkaline solution of step i is selected from the group consisting of an aqueous sodium sulfite solution and an aqueous sodium hydroxide solution.

18. The method of claim 15, wherein the agitation rate in the first reciprocating plate counter-current extraction column is between about 50 and 300 strokes per minute, the agitation rate in the second reciprocating plate counter-current extraction column is between about 100 and 400 strokes per minute, and the agitation rate in the third reciprocating plate counter-current extraction column is between about 100 and 400 strokes per minute.

19. The method of claim 1, wherein the acid catalyst of step h) is one or more members selected from the group consisting of sulfuric acid, sulfur trioxide, phosphoric acid, hydrochloric acid, boron trifluoride, and p-toluene sulfonic acid.

20. The method of claim 19, wherein the acid catalyst is sulfur trioxide.

21. The method of claim 1, including employing said method to produce DCL having a purity of greater than about 94%.

22. The method of claim 8, further including the step of recovering methyl isobutyl ketone from the lean caustic stream generated in step g) and from the decomposition stream in step i) for recycle.

23. The method of claim 1, wherein the organic solvent in the first cold extraction stream is removed before the decomposition step of step i).

24. The method of claim 1, further including the step of determining the composition of one or more streams selected from the group consisting of the oxidate, the first caustic extraction stream, the second caustic extraction stream, the first cold extraction stream, the second cold extraction stream, the first hot extraction stream, the second hot extraction stream, and the cleavage product of step h) by using proton magnetic resonance analysis.

25. The method of claim 24, wherein the stream being analyzed is selected from the group consisting of the oxidate, the first caustic extraction stream, the second caustic extraction stream, the first cold extraction stream, second cold extraction stream, the first hot extraction stream and the second hot extraction stream and the proton magnetic resonance analysis comprises:

a) obtaining a proton magnetic resonance spectrum for a stream;

b) determining the integral of a peak representing each compound in the stream in the proton magnetic resonance spectrum;

c) dividing the integral of each peak by the number of hydrogens that give rise to each peak to obtain the mole fraction for each compound in the stream; and d) repeating steps a) through c) for each stream being analyzed.

26. The method of claim 25, wherein the stream being analyzed is selected from the group consisting of the first caustic extraction stream and the second caustic extraction stream, and further includes the step of extracting the caustic from the stream prior to performing the proton magnetic resonance analysis.

27. The method of claim 24, wherein the stream being analyzed is the cleavage product and the proton magnetic resonance analysis comprises:

a) adding an internal standard to the cleavage product;

b) obtaining a proton magnetic resonance spectrum for the cleavage product/methylene chloride mixture;

c) determining the weight of each analyte in the cleavage product according to the formula:

$$\text{weight of analyte} = (\text{weight internal standard})(N_s/N_a)(M_a/M_s)(A_a/A_s)$$

where $N_s$ = number of protons from internal standard (2 for methylene chloride)

$N_a$ = number of protons from analyte for the structure measured $M_s$ = molecular weight of standard (85 for methylene chloride)

$M_a$ = molecular weight of analyte $A_s$ = integral area of standard $A_a$ = integral area of analyte.

* * * * *